United States Patent [19]

Hankins et al.

[11] Patent Number: 4,957,440

[45] Date of Patent: Sep. 18, 1990

[54] PROCESS FOR PREPARING NONSHRINKING PORCELAIN OPAQUE COVERING FOR DENTAL APPLIANCES

[76] Inventors: Robert B. Hankins, 1011 W. 34th St., Austin, Tex. 78705; Reid B. Green, 1801 Wells Branch Pkwy., Apt. 409, Austin, Tex. 78728

[21] Appl. No.: 893,920

[22] Filed: Aug. 7, 1986

[51] Int. Cl.[5] .................. A61C 5/08; A61C 13/83; B29C 33/52

[52] U.S. Cl. .................. 433/201.1; 427/2

[58] Field of Search .................. 106/35; 433/218–233, 433/201.1; 427/2

[56] References Cited

U.S. PATENT DOCUMENTS

| | | | |
|---|---|---|---|
| 89,253 | 4/1869 | Streeter | 106/35 |
| 382,607 | 5/1888 | Head | 106/35 |
| 1,040,838 | 10/1912 | Alexander | 106/35 |
| 1,621,793 | 3/1927 | Kruger | 106/35 |
| 1,886,982 | 11/1932 | Simon | 106/35 |
| 2,165,466 | 7/1939 | Erdle | 433/218 X |
| 2,744,326 | 5/1956 | Chaiken et al. | 433/223 |
| 4,585,417 | 4/1986 | Sozio et al. | 433/218 X |

OTHER PUBLICATIONS

Claus, "The Development and Application of a Shoulder Porcelain for VMK® Metal-Ceramics," Dental Magazin, Sep. 1984.

Wiley et al., "Esthetic Porcelain Margins: A Modified Porcelain–Wax Technique," Prosthetic Dentistry, Nov. 1986.

*Primary Examiner*—Nancy A. B. Swisher

*Attorney, Agent, or Firm*—Arnold, White & Durkee

[57] ABSTRACT

A process for applying an opaque covering to the metal casting to a metal - ceramic restoration comprising mixing powdered opaque porcelain with molten wax, heating the resultant mixture to a temperature approximately 2° to 5° C. above the melting point of the wax and applying the heated mixture to a metal casting base of the dental restoration.

1 Claim, No Drawings

PROCESS FOR PREPARING NONSHRINKING PORCELAIN OPAQUE COVERING FOR DENTAL APPLIANCES

BACKGROUND OF THE INVENTION

1. Field of the Invention

This invention relates generally to the construction of dental appliances such as crowns and the like. Most specifically, it relates to materials useful as opaque coatings for the metal castings commonly employed in metal-ceramic dental restorations. 2. The Problem and Description of the Related Art A long-standing aesthetic problem for the wearers of metal-ceramic appliances has been "shadowing" at the gingival margin. This phenomenon is usually manifest as a dark line at the limit of the appliance, such limit commonly being at the same level as the gingival margin. This shadowing is caused by the fact that the opaques heretofore used in the fabrication of such appliances have a tendency to shrink and their edges to become rounded during the glaze firing of the piece. This makes it difficult to realize an accurate marginal finish and additionally allows the metal surface of the base casting to show through the porcelain at the margin, thereby effecting shadowing.

The conventional fabrication technique for a metal-ceramic dental restoration such as a crown begins with the preparation of the supporting tooth by the dentist. First, a shoulder is formed on the tooth to be restored. This shoulder will ultimately support the final installed appliance. A mold is then made of the prepared tooth and from the mold a die is fashioned which is then used to construct the restoration. Using the die, a metal casting is made which conforms exactly to the prepared supporting tooth.

Ultimately, the crown or other such piece is built-up on the metal casting using various dentine and enamel porcelains. However, because these porcelains are translucent, it is first necessary to apply an opaque to the metal casting to prevent its being visible through the outer porcelain layers. Various opaque porcelains for this purpose are well-known in the art. They are usually supplied as a powder which is mixed with distilled water so as to form a suspension or medium which can be applied to the metal casting with a brush. A number of "modelling liquids" are available for use in place of the distilled water to provide a suspension. These are commonly a mixture of distilled water and glycerin. Some include alcohol as a third component.

A principal disadvantage of this fabrication technique is shadowing at the margin or base edge of the restoration. This result obtains because the opaques of the prior art shrink during firing. As they shrink, they recede from the margin of the metal casting allowing the base metal to show through.

John W. McLean, in "The Science and Art of Dental Ceramics——Volume 2," Quintessence Publishing Co., 1980, at page 322 advocates three different techniques for preventing the shadowing caused by the metal casting in metal-ceramic appliances. They are: the platinum foil technique; direct porcelain firing using a refractory ceramic die; and the direct lift-off of porcelain from the shoulders. For the direct porcelain lift-off technique he suggests the use of a dental porcelain mixture comprising one third by weight of core porcelain and two thirds by weight of standard opaque porcelain. Although this porcelain mixture is sufficiently stable to preserve intact the finely modelled sharp edges of the device during firing, problems arise from the different coefficients of thermal expansion possessed by the two components.

Heinz Claus, in a publication entitled "The Development and Application of a Shoulder Porcelain for VMK ®Metal-Ceramics," Dental Magazin, Sept. 1984, Dental Magazin Verlagsgesellschaft mbH, West Germany, describes a material and a technique for constructing a porcelain margin on a dental appliance. The proprietary "shoulder porcelain" described is said to have a melting point approximately 120° C. higher than that of normal dentine porcelain and to have markedly better stability during firing.

The fabrication technique preferred by Claus includes a shortening of the metal casting which is then underlined with paint-on opaque and shoulder porcelain. This technique is said to allow light incident on the tooth to be passed into the prepared tooth underlying the appliance, thereby effectively eliminating the shadowing that would otherwise be caused by the completely light-impervious metal casting.

Shrinkage of shoulder porcelains, however, remains a problem. Thus, Claus states: "To then correct the remaining very slight gap at the margin that still results, despite the markedly reduced shrinkage of these Shoulder Porcelains, the application and firing that have already been described have again to be repeated. . . . Following this correction, the crown should be built-up in the usual way using [conventional]dentine and enamel porcelains, and then fired according to standard firing instructions. One last fine correction to the shoulder should be carried out together with the glaze firing."

SUMMARY OF THE INVENTION

The present invention comprises a novel dental porcelain preparation which exhibits practically no shrinkage upon firing. Because of this feature, metal-ceramic dental restorations can be fabricated which when installed form a practically invisible, neutrally-colored joint between the appliance and the prepared tooth. The nonshrinking porcelain preparation is readily made, and is preferably formulated using standard opaque porcelain powders. Its use obviates the need for grinding the appliance to obtain a good fit to the supporting tooth and ensures a restoration having no unsightly shadowing.

The porcelain preparations of the invention are a putty-like mixture of powdered dental porcelain and wax. It is important that sufficient wax be present to provide a firmness to the mixture but at the same time a plasticity which enables it to be shaped. In that regard the mixture may be heated to soften the wax and thereby increase its plasticity.

Conventional dental porcelains such as those formulated from mixtures of quartz, feldspar, and kaolin may be employed in the practice of the invention. As mentioned above, a preferred form of dental porcelain for the purposes of the invention is conventional opaque vacuum porcelain. This porcelain has sufficient opacity to substantially reduce the "shadowing" problem described earlier. Most preferably the porcelain will be such that after firing it has a coefficient of thermal expansion close to that of the metal used to form the underlying base casting of the restoration.

A preferred form of wax for the purposes of this invention is a type of wax used in the dental arts known as "undercut wax." Most preferably, this wax will be paraffin-based, have a relatively high melting point (above about 65° C.), be colorless, non-toxic, and not form bubbles when heated in admixture with porcelain powder to around 600° C.

It is contemplated that other types of waxes, including insect waxes, plant waxes, hydrocarbon waxes, synthetic waxes (e.g., Carbowax), and the like may also be used or adapted for use in the practice of the invention. In general, the wax should be capable of imparting the putty-like quality described earlier. It should also vaporize cleanly when the mixture is fired, without leaving a residue or staining the porcelain.

It is not fully understood why the porcelain/wax formulations of the invention display substantially no shrinkage of the porcelain when fired. It is contemplated that the wax does not react with the constituents in the porcelain mix, and that it remains with the mix long enough during the firing process to enable the mix to retain its desired original shape during the complete process. In general, it is preferred that the firing process be conducted in two heating steps. In the first step, the starting putty-like mixture is heated sufficiently to vaporize the wax from the mixture. In the second step, the mixture is heated at a temperature high enough to fire the mixture. Typical temperatures for the first step should be high enough to vaporize the wax and also cause the porcelain powder to undergo at least partial bonding or sintering so as to obtain a definite structure. Temperatures of about 600° C. have been found to be very effective, but it is apparent that temperatures below and above this value may be more suitable for particular porcelain powders and porcelain/wax mixtures. Temperatures for the final firing step may also vary somewhat, depending upon the composition of the porcelain/wax mixture.

A typical starting material for the present invention may comprise approximately 70% by weight conventional opaque vacuum porcelain and about 30% by weight wax of a type known in the art as "undercut wax." The material is applied at an elevated temperature (typically about 2–5° C.) above the melting point of the wax using a heated instrument such as that described in U.S. Pat. 4,301,357. Application is made to the margin or shoulder of a metal casting which has been pre-coated with conventional opaque. Following application of the material, the coated metal casting is heated or fired to approximately 600° C. This temperature is maintained for about 10 minutes to volatilize the wax. Following substantial removal of the wax by vaporization, the device is fired in a vacuum oven at approximately 980° C. for about 10 minutes at a pressure differential of approximately 28 inHg. The remainder of the appliance can then be built-up using the methods of the prior art.

The practice of this invention permits the fabrication of dental restorations with very accurate margins without the need for the grinding operations used in the methods of the prior art to obtain a good fit of the appliance to the supporting tooth. This results in aesthetically pleasing dental appliances which have no visible shadowing due to showing through of the underlying metal casting a the margin of the restoration.

Porcelain dental appliances, including those with a cast metal base, are commonly built-up layer-by-layer using various opaque, dentine, and enamel porcelains. These porcelains differ principally in their incorporation of different fillers and pigments such as titanium dioxide. Some even include fluorescent oxides to better mimic the properties of natural human teeth. Shrinkage of all these porcelains during firing is a problem for technicians fabricating such dental appliances. The practice of the present invention may be employed to advantage with all these porcelains to virtually eliminate the shrinkage which would otherwise obtain during the firing steps of the fabrication.

DESCRIPTION OF PREFERRED EMBODIMENT

A nonshrinking opaque embodying the present invention may be formulated as follows:

(a) heat approximately 0.88 pennyweight (1.37 grams) of undercut wax to about 72° C. to melt the wax. A particularly suitable wax has been found to be "Dr. Will's Undercut Filling Material" marketed by the J. F. Jelenko Dental Division (Armonk, N.Y. 10504) of Pennwalt Corporation (Philadelphia, Pa. 19102);

(b) when the wax has melted, add approximately 2.03 pennyweight (3.16 grams) of an opaque such as that described in U.S. Patent 4,170,823 and marketed by Ceramco, Inc. (E. Windsor, NJ 08520) as CERAMCO ®II PAINT-O-PAKE vacuum porcelain;

(c) thoroughly mix the powder with the molten wax to the consistency of putty and maintain the mixture at a temperature of about 72° C.

The use of the nonshrinking opaque disclosed above is illustrated by way of example in the fabrication of a metal-ceramic crown restoration as follows:

(a) a metal casting is prepared in the conventional manner using a die obtained from an impression of the tooth to be restored;

(b) the margin (base edge) of the metal casting is reduced slightly to withdraw the casting from the shoulder of the die;

(c) the casting is then coated with opaque formulated in the conventional manner with water or modelling liquid;

(d) using a heated dental instrument such as that described in U.S. Patent 4,301,357 at a temperature between about 70 and 75° C. apply the nonshrinking opaque to the margin of the casting so that it fills the gap between the casting and the die and extends approximately ½ millimeter onto the surface of the metal of the casting;

(e) place the coated substructure on a holding peg and heat it to approximately 600° C. for about 10 minutes to vaporize the wax in the mixture;

(f) following vaporization of the wax, heat the entire substructure in a vacuum oven at approximately 980° C. for about 10 minutes.

After the opaque-coated casting has been fired and cooled to room temperature, the fit of the device to the die may be checked, and if satisfactory, the remainder of the restoration can be fabricated using conventional dentine and enamel porcelains in the manner of the prior art.

It will be apparent to those skilled in the art that various modifications may be made in the use of this novel material. For example, a nonshrinking opaque may be used to coat the entire metal casting, thereby obviating the need for the conventional opaques. It has also been found that the nonshrinking nature of an opaque embodying the invention permits its use on metal castings without the need for shortening and/or underlining the casting at its base edge to avoid shadowing at the margin of the final installed appliance.

It is to be understood that many changes can be made in, for example, the exact proportions of the components used to formulate the nonshrinking porcelain preparation, the temperatures used in mixing, storing, applying, vaporizing the wax, and firing the porcelain, the particular porcelains and waxes employed and the method of use of the resulting preparation without departing from the scope of the appended claims.

What is claimed is:

1. A process for applying an opaque covering to the metal casting of a metal-ceramic dental restoration which comprises:

(a) mixing about 7 parts by weight powdered opaque porcelain with about 3 parts by weight molten wax;

(b) heating the resulting mixture to a temperature approximately 2 to 5° C. above the melting point of the wax used in forming the mixture;

(c) applying the heated mixture to a metal casting forming the base of a dental restoration using an instrument heated to a temperature approximately 2 to 5° C. above the melting point of the wax used in forming the mixture;

(d) substantially vaporizing the wax from the mixture by heating the coated casting to about 600° C. for about 10 minutes; and (e) firing the remaining porcelain in a vacuum oven at approximately 980° C. for about 10 minutes.

* * * * *